United States Patent [19]

Ehrmann et al.

[11] 4,438,131
[45] Mar. 20, 1984

[54] Ω-CYANO-1, Ω-DIPHENYL-AZAALKANE DERIVATIVES, THEIR PREPARATION AND DRUGS CONTAINING THEM

[75] Inventors: Oskar Ehrmann, Mannheim-Neuhermsheim; Manfred Raschack, Weisenheim am Sand; Josef Gries, Wachenheim; Rolf Kretzschmar, Gruenstadt; Hans D. Lehmann, Hirschberg; Ludwig Friedrich, Bruehl; Dirk Wuppermann, Freinsheim; Frank Zimmermann, Neustadt; Werner Seitz, Plankstadt; Hans J. Treiber, Bruehl; Ferdinand Dengel, Wilhelmsfeld; Wolfram Frank, Heidelberg; Hans-Georg Kurbjuweit, Weinheim-Hohensachsen; Claus D. Mueller, Viernheim, all of Fed. Rep. of Germany

[73] Assignee: BASF Aktiengesellschaft, Fed. Rep. of Germany

[21] Appl. No.: 363,501

[22] Filed: Mar. 30, 1982

[30] Foreign Application Priority Data

Apr. 10, 1981 [DE] Fed. Rep. of Germany ....... 3114497
Nov. 6, 1981 [DE] Fed. Rep. of Germany ....... 3144150

[51] Int. Cl.³ ................ A61K 31/335; A61K 31/275; C07C 121/78
[52] U.S. Cl. ................................ 424/278; 260/465 E; 424/282; 424/304; 549/365; 549/366; 549/442

[58] Field of Search ....... 549/365, 366, 442; 260/465 E; 424/278, 282, 304

[56] References Cited

U.S. PATENT DOCUMENTS 3,261,859 7/1966 Dengel et al. ............... 260/465 E
4,305,887 12/1981 Herrling ...................... 260/465 E

FOREIGN PATENT DOCUMENTS 916719 12/1972 Canada .
1202500 8/1970 United Kingdom .
1202750 8/1970 United Kingdom .
1367677 9/1974 United Kingdom .
1377209 12/1974 United Kingdom .

*Primary Examiner*—Dolph H. Torrence
*Attorney, Agent, or Firm*—Keil & Witherspoon

[57] ABSTRACT

ω-Cyano-1,ω-diphenyl-azaalkane derivatives of the formula I

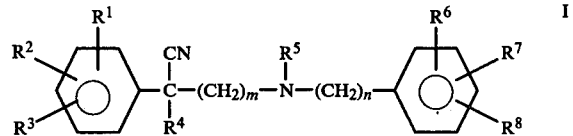

where $R^1$, $R^2$, $R^3$, $R^4$, $R^5$, $R^6$, $R^7$, $R^8$, m and n have the meanings given in the description, and salts thereof with physiologically tolerated acids, are useful in treating cardiovascular disorders.

15 Claims, No Drawings

ω-CYANO-1, ω-DIPHENYL-AZAALKANE DERIVATIVES, THEIR PREPARATION AND DRUGS CONTAINING THEM

The present invention relates to novel ω-cyano-1,ω-diphenyl-azaalkane derivatives, their preparation, and drugs containing these substances.

A number of 7-cyano-1,7-diphenyl-3-azaalkane derivatives have already been disclosed (cf. German Pat. No. 1,154,810). Verapamil (1,7-bis-(3,4-dimethoxyphenyl)-3-methylaza-7-cyano-8-methyl-nonane) and gallopamil (1-(3,4-dimethoxyphenyl)-3-methylaza-7-cyano-7-(3,4,5-trimethoxyphenyl)-8-methyl-nonane) have so far proved to be the most effective of these compounds.

We have now found novel compounds which are superior to verapamil and gallopamil.

The present invention relates to ω-cyano-1,ω-diphenyl-azaalkane derivatives of the formula I

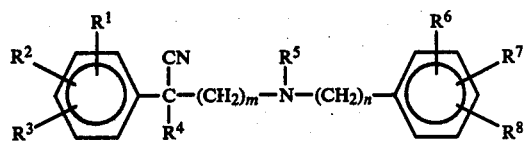

where $R^1$, $R^2$, $R^3$, $R^6$, $R^7$ and $R^8$ are identical or different and each is hydrogen, halogen, hydroxyl, trifluoromethyl, $C_1$–$C_4$-alkyl, nitro, $C_1$–$C_4$-alkoxy or $C_1$–$C_4$-alkylmercapto, and two radicals in adjacent positions can together form a methylenedioxy, ethylenedioxy or 1,3-dioxatetramethylene group, $R^4$ is straight-chain or branched, saturated or unsaturated alkyl of 9 to 20 carbon atoms, $R^5$ is hydrogen or $C_1$–$C_4$-alkyl and m and n are identical or different and each is from 2 to 4, and salts thereof with physiologically tolerated acids.

Examples of suitable physiologically tolerated acids are hydrochloric acid, sulfuric acid, phosphoric acid, acetic acid, malonic acid, succinic acid, fumaric acid, maleic acid, citric acid, tartaric acid, lactic acid, amidosulfonic acid and oxalic acid.

$R^1$, $R^2$, $R^3$, $R^6$, $R^7$ and $R^8$ are preferably hydrogen or alkoxy, in particular methoxy, $R^4$ is preferably straight-chain alkyl of 10 to 14, in particular 11 to 13, carbon atoms and $R^5$ is preferably methyl.

The novel compounds have an asymmetric carbon atom and can therefore be prepared in the form of their antipodes, cf. German Pat. Nos. 2,059,923 and 2,059,985.

The novel compounds are prepared by a process wherein (a) a phenylacetonitrile of the formula II

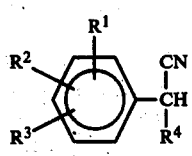

where $R^1$, $R^2$, $R^3$ and $R^4$ have the above meanings, is reacted with a 1-phenylazaalkane of the formula III

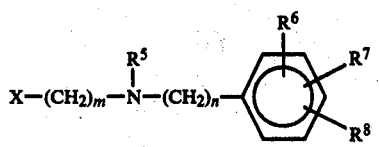

where $R^5$, $R^6$, $R^7$, $R^8$, m and n have the above meanings and X is a leaving group, or (b) an ω-cyano-1,ω-diphenyl-azaalkane derivative of the formula IV

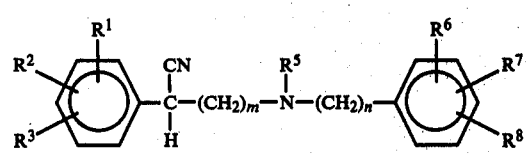

where $R^1$, $R^2$, $R^3$, $R^5$, $R^6$, $R^7$, $R^8$, m and n have the above meanings, is reacted with a compound of the formula V $$R^4-Y \qquad V$$

where $R^4$ has the above meanings, and Y is a leaving group, or (c) a phenylacetonitrile of the formula VI

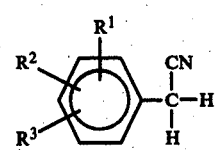

where $R^1$, $R^2$ and $R^3$ have the above meanings, is reacted with a 1-phenylazaalkane of the formula III and a compound of the formula V, or (d) a phenylacetonitrile of the formula VII

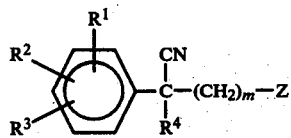

where $R^1$, $R^2$, $R^3$, $R^4$ and m have the above meanings and Z is a leaving group, is reacted with a phenylalkylamine of the formula VIII

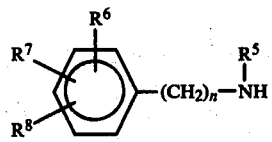

where $R^5$, $R^6$, $R^7$, $R^8$ and n have the above meanings, or (e) an ω-amino-alkyl-phenylacetonitrile of the formula IX

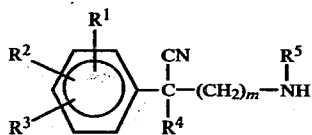

where $R^1$, $R^2$, $R^3$, $R^4$, $R^5$ and m have the above meanings, is reacted with a phenylalkyl derivative of the formula X

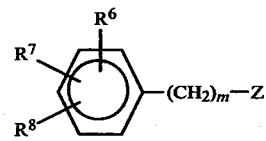

where $R^6$, $R^7$, $R^8$, m and Z have the above meanings, or (f) an ω-cyano-1,ω-diphenyl-azaalkane derivative of the formula XI

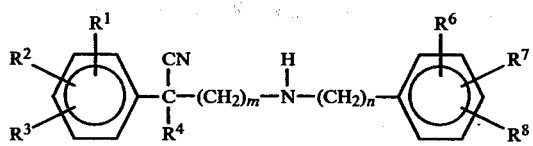

where $R^1$, $R^2$, $R^3$, $R^4$, $R^6$, $R^7$, $R^8$, m and n have the above meanings, is alkylated, or (g) an ω-amino-alkyl-phenylacetonitrile of the formula IX is reacted with an aldehyde of the formula XII

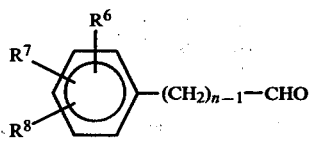

where $R^6$, $R^7$, $R^8$ and n have the above meanings, under reducing conditions, or (h) an aldehyde of the formula XIII

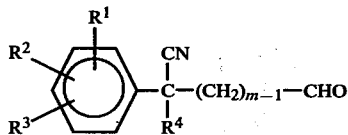

where $R^1$, $R^2$, $R^3$, $R^4$ and m have the above meanings, is reacted with a phenylalkylamine of the formula VIII under reducing conditions, and, if desired and if one or more of $R^1$, $R^2$, $R^3$, $R^6$, $R^7$ and $R^8$ are alkoxy, the resulting compound is subjected to ether cleavage, and/or, if desired, the resulting compound is converted into a salt with a physiologically tolerated acid.

Reaction (a) can be carried out, for example, by metallizing a CH-acid phenylacetonitrile of the formula II with a base in an inert solvent and reacting the product with a compound of the formula III. Where appropriate, it is also possible to add the base to a solution of compounds of the formula II and III.

Suitable bases include alkali metal hydrides, hydroxides, alcoholates and amides, and organometallic compounds. Preferred based are sodium amide powder or suspension, potassium hydroxide powder, butyl-lithium and lithium diisopropylamide.

Suitable solvents for the reaction include aromatic and aliphatic hydrocarbons, as well as higherboiling aliphatic ethers and dipolar aprotic solvents. Toluene is preferably used.

Reaction (a) can also be carried out under phase transfer catalysis. Suitable catalysts are quaternary ammonium and phosphonium salts and crown ethers.

The reaction temperature depends on the base used. For example, if butyl-lithium is used, the reaction is carried out at from 0° to −100° C., and if sodium amide is used, a temperature of from 50° to 150° C. is preferred.

The reaction of a compound of the formula IV with a compound of the formula V to give a compound according to the invention (process b) is carried out in a manner similar to that for process (a).

Examples of suitable reactants of the formula IV are alkane derivatives with a leaving group, such as halides, sulfuric acid esters, tosylates, mesylates or triflates.

In process (c), any desired sequence of addition of the compounds III, V and VI can be chosen, and the intermediates do not have to be isolated.

Reaction (d) is carried out by simply heating the reactant, preferably to 120°–180° C. A solvent can also be used, but is not necessary. The same applies to reaction (e). In both cases, a suitable leaving group Z is halogen, preferably chlorine or bromine.

The alkylation (f) is effected with a dialkyl sulfate or alkyl halide in the presence of an acid acceptor, eg. triethylamine or potassium carbonate, advantageously in the presence of a solvent, such as toluene or a dipolar aprotic solvent, eg. dimethylformamide. Methylation can also be carried out by the method of Leuckart-Wallach, using formaldehyde/formic acid.

In processes (g) and (h), the two reactants of the formulae IX and XII or XIII and VII respectively are condensed under reducing conditions.

Suitable solvents include aliphatic and aromatic hydrocarbons, halohydrocarbons, ethers, alcohols and lower fatty acids. The reaction temperatures are from 0° to 150° C., preferably from 20° to 70° C.

Suitable reducing agents include hydrogen in the presence of a catalyst, eg. $PtO_2$, Pd/C or a nickel or cobalt catalyst, nascent hydrogen obtained from a metal and an acid, complex metal hydrides (eg. $NaBH_4$) and hydride donors (eg. formic acid).

If a catalyst is present, the reduction is preferably carried out under atmospheric pressure.

Reactions (a) to (h) have been disclosed in German Pat. Nos. 1,154,810, 1,158,083 and 2,059,923, German Published Application DAS No. 2,263,527, German Pat. No. 2,631,222 and German Laid-Open Application DOS No. 3,034,221.

Those starting materials of the formulae IV, VII, IX, X, XI and XIII which have not yet been described can be prepared as follows:

The compounds IV are obtained by reacting a phenylacetonitrile (VI) with a 1-phenyl-ω-haloazaalkane (cf. III) in the presence of sodium amide in toluene.

The compound VII can be prepared by reacting a 1-cyano-1-phenyl-alkane (II) with chloropropanol and then reacting the resulting alcohol with, for example, thionyl chloride.

The compounds IX are obtained by reacting a phenylacetonitrile derivative VII with an alkylamine.

The substances of the formula X are prepared, for example, by hydrolyzing a phenylacetonitrile VI to phenylacetic acid, reducing the latter and chlorinating the resulting alcohol, for example with thionyl chloride.

The compounds XI are obtained by reacting a 1-cyano-1-phenyl-alkane (II) with a 1-phenyl-ω-haloazaalkane (cf. III) in the presence of sodium amide in toluene.

The compounds XIII are obtained by reacting a 1-cyano-1-phenyl-alkane (II) with an ω-haloaldehyde diethyl acetal in the presence of sodium amide in toluene and then treating the resulting product with acid.

Hydroxy-substituted ω-cyano-1,ω-diphenyl-azaalkane derivatives of the formula I can be obtained from the corresponding alkoxy derivatives by ether cleavage, which can be carried out using concentrated hydrobromic acid, a boron trihalide (chloride or bromide) or an alkali metal mercaptide in a dipolar aprotic solvent.

The novel compounds are useful in treating serious functional disorders of the cardiovascular system as well as cardiomyopathies and angiopathies. They have a cardio-protective action in cases of hypoxic and ischemic heart disease, non-coronarogenic myocardial damage, tachycardia and arrhythmia. Because of the antihypertensive and antiaggregating components of their action, they can also be used for treating high blood pressure and circulatory disorders. They relax the smooth muscle, and can therefore be used, for example, for relaxing spasms of the vessels, the bronchi, the ureter and the gastrointestinal tract, as well as for tocolysis. Furthermore, they inhibit secretory processes, which play a part, for example, in ulcerogenesis (release of acid), as well as inhibiting allergic reactions. The novel compounds are very effective when administered orally, and have a long-lasting action.

The following methods were used to demonstrate the pharmacological actions:

1. Antihypertensive action

The substances were administered orally to male spontaneously hypertensive rats (SHR) of the Okamoto strain (weight: 300–400 g). The systolic blood pressure was determined non-operatively on the tails of the rats by piezo-crystal measurements before and 2, 6, 24 and, where relevant, 30 hours after administration.

The dose which reduced the systolic pressure by 20%, taking into consideration the values from untreated control animals, was taken as the ED 20%.

Verapamil was used as the comparative substance.

2. Antiarrhythmic action

To determine the antiarrhythmic activity, the substances were administered orally to rats (Sprague-Dawley, weight: 200–250 g). 5 hours later, the animals were anesthetized with sodium thiobutabarbital (100 mg/kg i.p.). Aconitine was infused intravenously (dosage rate: 0.005 mg/kg.minute) as the arrhythmogenic substance 6 hours after administration of the drug. After 2.74±0.07 minutes, the ECGs of the untreated animal showed arrhythmias, the onset of which can be delayed dose-dependently by antiarrhythmic drugs.

The relative lengthening of the aconitine infusion period (Δ%) by a dosage of in each case 46.4 mg/kg of the test substances was determined.

Verapamil was used as the comparative substance.

3. Cardio-protective action against hypoxic cardiac metabolism disorders

A drastic depletion of energy-rich phosphates in the mycocardium of anesthetized rats (Wistar, weight: 250–350 g, anesthetic: thiobutabarbital 100 mg/kg i.p.) was produced by standardized respiration with an oxygen-deficient mixture (2% of $O_2$). The creatine phosphate was determined, using the freezestopping technique (liquid nitrogen), in muscle samples from the apex of the heart by the method of Lamprecht et al., 1974 (Lamprecht, W., P. Stein, F. Heinz and H. Weisser: Creatine phosphate, in: Bergmeyer, H. U., Methoden der enzymatischen Analyse, Verlag Chemie, Weinheim, 2 (1974), 1825–1829).

The test substances were administered to the still conscious animals 6 hours before the oxygen-deficient respiration. The percentage difference between the creatine phosphate concentration in the myocardium of animals pretreated with the test substance and that of the untreated hypoxic control animals was determined.

Verapamil was used as the comparative substance.

4. Platelet aggregation-inhibiting action

The substances were administered orally to male Sprague-Dawley rats (200–250 g). 1 hour after administration, samples of blood were taken under ether anesthetic, and platelet-rich plasma was obtained by centrifugation (300 g, 10 minutes at 4° C.). The platelet aggregation was measured photometrically, with the addition of $MgCl_2$ and (end concentration of 10 mmoles/l) and Collagen Stago (end concentration of 0.02 mg/ml), in a Mark 3 Born Aggregometer. The maximum change in extinction/second was used as a measure of the aggregation.

The dose which inhibits the collagen-induced platelet aggregation by 33% was taken as the ED 33%.

Verapamil was used as the comparative substance.

5. Antiallergic action

The model of passive cutaneous anaphylaxis (PCA) was used for this test.

Anesthetized male rats (100–140 g) were sensitized by intradermal injection (shaven dorsal skin) of 0.1 ml of an ovalbumin antiserum. After a sensitizing period of about 48 hours, they were treated with the test substances (oral administration). After various latency periods (2, 6, 12 and 24 hours), the experimental animals were injected intravenously with an antigen/Evans blue solution. The animals were sacrificed in each case 30 minutes after the injection, and the dorsal skin was removed and the circular blue stain on the inner surface measured.

The antiallergic action was quoted as the relative inhibition (Δ%) of the diameter of the colored spot. Verapamil was used as the comparative substance.

TABLE 1

| Antihypertensive action, spontaneously hypertonic rats (SHR), peroral administration | | | | |
|---|---|---|---|---|
| Substance from Example No. | Lowering of systolic blood pressure ED 20% (mg/kg)[1] | | | |
| | 2 hrs. | R.A.[2] | 6 hrs. | R.A.[2] | 24 hrs. |
| 3 | 24.9 | 0.93 | 14.1 | 1.46 | 18.7 |
| 19 | 7.5 | 3.09 | 19.8 | 1.04 | 46.4 |
| 20 | 3.7 | 6.27 | 6.6 | 3.12 | 12.5 |
| 25 | 6.8 | 3.41 | 10.2 | 2.02 | 46.4 |
| 42 | 0.3 | 2.25 | | | 58.3 |
| Verapamil | 23.2 | 1.00 | 20.6 | 1.00 | — |

[1]Dose which reduces the systolic blood pressure by 20%.
[2]R.A. = Relative activity; verapamil = 1.00

TABLE 2

Antiarrhythmic action, rats, dose: 46.4 mg/kg, oral administration

| Substance from Example No. | Lengthening of the aconitine infusion time (Δ%) |
|---|---|
| 3 | 122 |
| 5 | 107 |
| 7 | 88 |
| 8 | 88 |
| 12 | 128 |
| 13 | 188 |
| 14 | 98 |
| 15 | 88 |
| 16 | 61 |
| 19 | 50 |
| 23 | 86 |
| 24 | 68 |
| 25 | 186 |
| 46 | 54 |
| 47 | 104 |
| 53 | 63 |
| 58 | 53 |
| 59 | 61 |
| 61 | 69 |
| 62 | 86 |
| 63 | 70 |
| 67 | 65 |
| 70 | 59 |
| 72 | 96 |
| 75 | 71 |
| Verapamil | 29[1] |

[1] not significant

TABLE 3

Cardio-protective action 6 hours after oral administration to rats.

| Substance from Example No. | Dose with maximum effect, mg/kg | Creatine phosphate concentration in the myocardium, deviation from the control, in % |
|---|---|---|
| 3 | 40 | +77 |
| 5 | 20 | +69 |
| 7 | 40 | +49 |
| 8 | 40 | +35 |
| 10 | 40 | +35 |
| 16 | 40 | +50 |
| 17 | 40 | +51 |
| 19 | 2 | +38 |
| 20 | 5 | +38 |
| 67 | 40 | +53 |
| 72 | 40 | +38 |
| 75 | 20 | +80 |
| Verapamil | 40 | +9[1] |

[1] not significant

TABLE 4

Platelet aggregation-inhibiting action 1 hour after oral administration to rats

| Substance from Example No. | Inhibition of aggregation, ED 33% (mg/kg) (1) |
|---|---|
| 3 | 9.6 |
| 6 | 49 |
| 70 | 119 |
| 75 | 90.2 |
| Verapamil | (2) |

(1) Dose which inhibits collagen-induced platelet aggretation by 33%.
(2) A dose of 46.4 mg/kg has no antiaggregating action.

TABLE 5

Antiallergic action after oral administration of 21.5 mg/kg of test substance. PCA rats. Investigation of the period of action.

| Substance from Example No. | % inhibition Latency period in hours | | | |
|---|---|---|---|---|
| | 2 | 6 | 12 | 24 |
| 3 | 15 | 40 | 83 | 68 |
| Verapamil | 53 | 50 | 33 | 31 |

The compounds according to the invention have the following actions:

1. Antihypertensive action

The antihypertensive action of the compounds according to the invention on SH rats (Table 1) is generally more pronounced than that of verapamil. There is also a significant increase in the period of action. In contrast to verapamil, which was ineffective at the sublethal dose of 100 mg/kg after 24 hours, the other substances (in particular those from Examples 3 and 20) still have an antihypertensive action at this point in time.

2. Antiarrhythmic action

The compounds according to the invention listed in Table 2 lengthen the aconitine infusion period by from 50% (Example 19) to 188% (Example 13).

They thus differ clearly from verapamil, which has no significant effect on aconitine-induced arrhythmias in rats in a dose of 46.4 mg/kg.

3. Cardio-protective action

The Examples summarized in Table 3 show that oral doses of 2–40 mg/kg of the compounds according to the invention have a significant cardio-protective action.

The compounds from Examples 3, 5 and 68 have a particularly powerful action. Under the same experimental conditions, verapamil provides no significant protective action up to the maximum tolerable oral dose of 40 mg/kg.

4. Platelet aggregation-inhibiting action

Of the novel compounds, those from Examples 3, 63 and 68 stand out by virtue of a detectable inhibiting action on collagen-induced platelet aggregation on oral administration to rats (Table 4). Under the same experimental conditions, the maximum tolerated dose of verapamil of 46.4 mg/kg still has no effect on platelet aggregation.

5. Antiallergic action

On the model of passive cutaneous anaphylaxis in rats, the compound according to the invention (Example 3) has a long-lasting antiallergic action after oral administration (Table 5). Investigation of the period of action showed that the compound has a substantially more powerful action after latency periods of 12 and 24 hours than the comparison compound verapamil, and therefore has a comparatively longer period of action.

The novel compounds can be administered orally or parenterally in a conventional manner.

The dosage depends on the age, condition and weight of the patient and on the route of administration. As a rule, the daily dose of active compound is from about 0.1 to 10 mg/kg of body weight in the case of oral administration, and from 0.01 to 1.0 mg/kg of body weight in the case of parenteral administration. In normal cases, the daily doses administered are from 1 to 5 mg/kg orally or from 0.05 to 0.25 mg/kg parenterally.

The novel compounds may be employed in the conventional solid or liquid pharmaceutical forms, such as tablets, film tablets, capsules, powders, granules, dragees, suppositories, solutions or metered aerosols. These are prepared in a conventional manner, and for this purpose the active compounds can be mixed with the conventional pharmaceutical auxiliaries, such as tablet binders, fillers, preservatives, tablet disintegrating agents, flow control agents, plasticizers, wetting agents, dispersants, emulsifiers, solvents, retardants and/or antioxidants (cf. H. Sucker, P. Fuchs and P. Speiser: Pharmazeutische Technologie, Thieme-Verlag, Stuttgart). The formulations thus obtained normally contain from 0.1 to 99% by weight of the active compound.

The Examples which follow illustrate the invention. Thin-layer chromatography was carried out with Silica Gel 60 F 254 on TLC plates with a concentration zone (from E. Merk).

EXAMPLE 1

1,7-bis-(3-Ethoxyphenyl)-3-methylaza-7-cyano-nonadecane 20.4 g (0.06 mole) of 1-cyano-1-(3-ethoxyphenyl)-tridecane (prepared by phase transfer-catalyzed alkylation of 3-ethoxyphenylacetonitrile with 1-bromododecane) and 16.9 g (0.06 mole) of 1-chloro-4-methylaza-6-(3-ethoxyphenyl)-hexane [prepared from N-methyl-$\beta$-(3-ethoxyphenyl)-ethylamine and 1-bromo-3-chloropropane by a method similar to that described in Arzneim.-Forsch. 28 (II) (1978), 2048] were dissolved in 100 ml of dry toluene in a three-necked flask provided with a stirrer, dropping funnel, reflux condenser and thermometer. 9.3 g (0.07 mole) of a 30% strength suspension of sodium amide in toluene were then added dropwise at from 100° to 110° C., with stirring, and stirring was continued under reflux for a further 90 minutes.

The resulting reaction solution was poured into 200 ml of ice-water, and the toluene phase was separated off and washed twice with water. The required amount of hydrochloric acid was added to the toluene solution, the toluene was distilled off under reduced pressure and the residue which remained was recrystallized from acetone to give 29.7 g (82%) of the hydrochloride of melting point 132°–134° C.

The compounds which follow were obtained in a similar manner:

2. 1,7-bis-(2-Methoxyphenyl)-3-methylaza-7-cyano-nonadecane hydrochloride of melting point 60°–69.5° C.
3. 1,7-bis-(3-Methoxyphenyl)-3-methylaza-7-cyano-nonadecane hydrogen oxalate of melting point 97°–98° C. The melting point of the hydrochloride monohydrate is 60°–60.5° C.
4. 1,7-bis-(4-Methoxyphenyl)-3-methylaza-7-cyano-nonadecane hydrochloride of melting point 114°–116° C.
5. 1,7-Diphenyl-3-methylaza-7-cyano-nonadecane hydrochloride of melting point 112°–115° C.
6. 1,7-bis-(3-Methoxyphenyl)-3-methylaza-7-cyano-docosane hydrogen oxalate of melting point 100°–102° C.
7. 1-Phenyl-3-methylaza-7-cyano-7-(3-methoxyphenyl)-nonadecane hydrogen oxalate of melting point 91°–93° C.
8. 1-(3-Methoxyphenyl)-3-methylaza-7-cyano-7-phenyl-nonadecane hydrogen oxalate of melting point 100°–102° C.
9. 1,7-bis-(3-Ethoxyphenyl)-3-methylaza-7-cyano-docosane hydrochloride of melting point 110°–113° C.
10. 1,7-Diphenyl-3-methylaza-7-cyano-hexadecane hydrochloride of melting point 109°–111° C.
11. 1-(3-Methoxyphenyl)-3-methylaza-7-cyano-7-phenyl-hexadecane.
   Analysis: Calculated: C 71.3; H 8.6; N 5.2. Found: C 71.1; H 8.6; N 5.2.
12. 1-Phenyl-3-methylaza-7-cyano-7-(3-methoxyphenyl)-hexadecane
   Analysis: Calculated: C 71.3; H 8.6; N 5.2. Found: C 71.0; H 8.6; N 5.3.
13. 1,7-bis-(3-Methoxyphenyl)-3-methylaza-7-cyano-hexadecane
   Analysis: Calculated: C 69.7; H 8.5; N 4.9. Found: C 69.7; H 8.5; N 5.0.
14. 1-(3-Chlorophenyl)-3-methylaza-7-cyano-7-(3-methoxyphenyl)-nonadecane hydrochloride monohydrate of melting point 68°–71° C.
15. 1-(3-Methoxyphenyl)-3-methylaza-7-cyano-7-(4-chlorophenyl)-nonadecane.
   Analysis: Calculated: C 75.5; H 9.4; N 5.3; Cl 6.8. Found: C 75.5; H 9.4; N 5.3; Cl 6.6.
16. 1-(3-Methoxyphenyl)-3-methylaza-7-cyano-7-(1,3-benzodioxan-6-yl)-nonadecane
   Analysis: Calculated: C 76.6; H 9.6; N 5.1. Found: C 76.6; H 9.6; N 5.2.
17. 1-Phenyl-3-methylaza-7-cyano-7-(1,3-benzodioxan-6-yl)-nonadecane
   Analysis: Calculated: C 78.7; H 9.7; N 5.4. Found: C 78.4; H 9.7; N 5.5.
18. 1-(3-Methoxyphenyl)-3-methylaza-7-cyano-7-(3-trifluoromethyl-phenyl)-nonadecane
   Analysis: Calculated: C 73.0; H 8.8; N 5.0. Found: C 73.1; H 8.8; N 5.0.
19. 1-(3-Methoxyphenyl)-3-methylaza-7-cyano-7-(3,4-dimethoxyphenyl)-nonadecane hydrochloride of melting point 96°–98° C.
20. 1-(3-Methoxyphenyl)-3-methylaza-7-cyano-7-(3,4,5-trimethoxyphenyl)-nonadecane hydrochloride of melting point 93°–95° C.
21. 1,7-bis-(3-Chlorophenyl)-3-methylaza-7-cyano-nonadecane
   Analysis: Calculated: C 72.6; H 8.8; N 5.3; Cl 13.4. Found: C 72.8; H 8.6; N 5.5; Cl 13.4.
22. 1-(3-Methoxyphenyl)-3-methylaza-7-cyano-7-(3-chlorophenyl)-nonadecane
   Analysis: Calculated: C 75.5; H 9.4; N 5.3; Cl 6.8. Found: C 75.6; H 9.4; N 5.3; Cl 6.8.
23. 1-(3-Methoxyphenyl)-3-methylaza-7-cyano-7-(3,4-ethylenedioxyphenyl)-nonadecane
   Analysis: Calculated: C 76.6; H 9.6; N 5.1. Found: C 76.4; H 9.3; N 5.1.
24. 1-(3-Methoxyphenyl)-3-methylaza-7-cyano-7-(3-tolyl)-nonadecane
   Analysis: Calculated: C 80.9; H 10.4; N 5.5. Found: C 80.6; H 10.1; N 5.5.
25. 1,7-bis-(3-Methoxyphenyl)-3-methylaza-7-cyano-octadecane
   Analysis: Calculated: C 78.2; H 9.9; N 5.5. Found: C 78.1; H 9.8; N 5.5.
26. 1,7-bis-(3-Methoxyphenyl)-3-methylaza-7-cyano-8-(n-butyl)-dodecane
   Analysis: Calculated: C 77.8; H 9.7; N 5.9. Found: C 77.8; H 9.7; N 5.9.
27. 1,7-bis-(3-Methoxyphenyl)-3-methylaza-7-cyano-8-(n-pentyl)-tridecane
   Analysis: Calculated: C 78.2; H 9.9; N 5.5. Found: C 78.2; H 10.0; N 5.4.

28. 1,7-bis-(3-Methoxyphenyl)-3-methylaza-7-cyano-8-(n-hexyl)-tetradecane
Analysis: Calculated: C 78.6; H 10.2; N 5.2. Found: C 78.7; H 9.8; N 5.2.

29. 1-(3-Methoxyphenyl)-3-methylaza-7-cyano-7-(3-n-butoxyphenyl)-nonadecane
Analysis: Calculated: C 78.9; H 10.4; N 5.0. Found: C 78.8; H 10.5; N 5.2.

30. 1-(3-n-Butoxyphenyl)-3-methylaza-7-cyano-7-(3-methoxyphenyl)-nonadecane
Analysis: Calculated: C 78.9; H 10.4; N 5.0. Found: C 78.8; H 10.3; N 5.1.

31. 1,7-bis-(3-n-Butoxyphenyl)-3-methylaza-7-cyano-nonadecane hydrochloride of melting point 127°–129° C.

32. 1,7-Bis-(3-methoxyphenyl)-3-methylazo-7-cyano-17-octadecene
Analysis: Calculated: C 78.5; H 9.6; N 5.5. Found: C 78.7; H 9.6; N 5.4.

33. 1-(3-Methoxyphenyl)-3-methylaza-7-cyano-7-(3-fluorophenyl)-nonadecane
Analysis: Calculated: C 77.9; H 9.7; N 5.5. Found: C 78.0; H 9.7; N 5.5.

34. 1-(3-Fluorophenyl)-3-methylaza-7-cyano-7-(3-methoxyphenyl)-nonadecane
Analysis: Calculated: C 77.9; H 9.7; N 5.5. Found: C 78.0; H 9.6; N 5.4.

35. 1,7-bis-(3-Fluorophenyl)-3-methylaza-7-cyano-nonadecane
Analysis: Calculated: C 77.4; H 9.3; N 5.6. Found: C 77.2; H 9.3; N 5.6.

36. 1-(3-Methoxyphenyl)-3-methylaza-7-cyano-7-(3-tert.-butoxyphenyl)-nonadecane
Analysis: Calculated: C 79.0; H 10.4; N 5.0. Found: C 78.8; H 10.3; N 4.9.

37. 1-(3-tert.-Butoxyphenyl)-3-methylaza-7-cyano-7-(3-methoxyphenyl)-nonadecane
Analysis: Calculated: C 79.0; H 10.4; N 5.0. Found: C 78.9; H 10.5; N 5.0.

38. 1,7-bis-(3-tert.-Butoxyphenyl)-3-methylaza-7-cyano-nonadecane
Analysis: Calculated: C 79.4; H 10.7; N 4.6. Found: C 79.5; H 10.6; N 4.7.

The compounds which follow can be obtained in an analogous manner:

39. 1-(4-tert.-Butylphenyl)-3-methylaza-7-cyano-7-(3-methoxyphenyl)-nonadecane
40. 1-(4-Fluorophenyl)-3-methylaza-7-cyano-7-(3-methoxyphenyl)-nonadecane
41. 1-(3,4-Dimethoxyphenyl)-3-methylaza-7-cyano-7-(4-bromophenyl)-eicosane
42. 1-(4-Ethylmercaptophenyl)-3-methylaza-7-cyano-7-(3-methoxyphenyl)-nonadecane
43. 1,7-bis-(3-Methylmercaptophenyl)-3-methylaza-7-cyano-nonadecane.
44. 1-(3,4-Dichlorophenyl)-3-methylaza-7-cyano-7-(3-methoxyphenyl)-nonadecane.
45. 1-(3-Fluorophenyl)-3-methylaza-7-cyano-7-(3-chlorophenyl)-nonadecane

EXAMPLE 46

1,7-bis-(3,4-Dimethoxyphenyl)-3-methylaza-7-cyano-nonadecane 34.5 g (0.1 mole) of α-dodecylveratryl cyanide were dissolved in 15 ml of toluene at 40° C. in a three-necked flask provided with a stirrer, dropping funnel and reflux condenser. 26 g of potassium hydroxide powder and 0.2 g of tetrabutylammonium iodide were added to this solution. A solution of 27 g (0.1 mole) of N-methyl-N-homoveratryl-amino-γ-chloropropane in 20 ml toluene was then added, with stirring, at a rate such that the temperature did not exceed 90° C. After the addition, stirring was continued at this temperature for a further 2.5 hours. The cooled reaction mixture was washed with 100 ml of water and the solvent was distilled off to give 55 g of end product in the form of a yellow oil. The melting point of the hydrogen oxalate is 93°–96° C.

The compounds which follow were obtained in a similar manner:

47. 1-(3,4-Dimethoxyphenyl)-3-methylaza-7-cyano-7-(3-chlorophenyl)-nonadecane
Analysis: Calculated: C 73.5; H 9.3; N 5.0; Cl 6.4. Found: C 73.6; H 9.3; N 5.0; Cl 6.4.

48. 1-(3,4-Dimethoxyphenyl)-3-methylaza-7-cyano-7-(1,3-benzodioxan-6-yl)-nonadecane
Analysis: Calculated: C 74.7; H 9.4; N 4.8. Found: C 74.6; H 9.2; N 4.9.

49. 1-(3,4-Dimethoxyphenyl)-3-methylaza-7-cyano-7-(3,4,5-trimethoxyphenyl)-nonadecane amidosulfonate of melting point 99°–102° C.

50. 1-(3,4-Dimethoxyphenyl)-3-methylaza-7-cyano-7-(3-ethoxyphenyl)-docosane hydrochloride of melting point 109°–112° C.

51. 1-(3,4-Dimethoxyphenyl)-3-methylaza-7-cyano-7-(3-ethoxyphenyl)-nonadecane hydrochloride of melting point 111°–113° C.

52. 1-(3,4-Dimethoxyphenyl)-3-methylaza-7cyano-7-(3,4,5-trimethoxyphenyl)-pentacosane hydrochloride of melting point 98°–101° C.

53. 1-(3,4-Dimethoxyphenyl)-3-methylaza-7-cyano-7-(3,4,5-trimethoxyphenyl)-heptadecane amidosulfonate of melting point 97°–100° C.

EXAMPLE 54

1,6-bis-(3,4-Dimethoxyphenyl)-3-ethylaza-6-cyano-octadecane 45.2 g (0.1 mole) of α-(n-dodecyl)-α-(2-bromoethyl)-3,4-dimethoxyphenyl-acetonitrile (obtained by condensation of α-dodecyl-3,4-dimethoxy-phenylacetonitrile with 1,2-dibromoethane in toluene solution in the presence of lithium diisopropylamide) and 41.8 g of β-(N-ethyl)-3,4-dimethoxyphenethylamine were heated at 150° C. in an oilbath for two hours. 250 ml of toluene were added while the mixture was still hot and the precipitate of β-(N-ethyl)-3,4-dimethoxy-phenethylamine hydrobromide which separated out was filtered off with suction.

The filtrate was washed with 2 N sodium hydroxide solution and the base was then extracted by shaking with methanolic aqueous amidosulfonic acid and the latter was washed several times with ether. The base was liberated by addition of potassium carbonate solution and was taken up in ether, and the solution was dried with anhydrous potassium carbonate. The solvent was distilled off to give 42 g (72%) of a viscous yellow oil, which was purified by column chromatography (silica gel, ethyl acetate).

Analysis: Calculated: C 74.4; H 9.7; N 4.8. Found: C 74.3; H 9.6; N 4.8.

The compounds which follow were obtained in a similar manner:

55. 1,7-bis-(3,5-di-n-Butoxyphenyl)-3-methylaza-7-cyano-nonadecane
Analysis: Calculated: C 76.9; H 10.8 N 3.7. Found: C 76.9; H 10.9; N 4.0.

56. 1,7-bis-(3,5-di-Isopropoxyphenyl)-3-methylaza-7-cyano-nonadecane

Analysis: Calculated: C 76.2; H 10.5; N 4.0. Found: C 76.3; H 10.4; N 4.0.

57. 1,7-bis-(3,5-di-n-Propoxyphenyl)-3-methylaza-7-cyano-nonadecane

Analysis: Calculated: C 76.3; H 10.5; N 4.0. Found: C 76.4; H 10.4; N 4.0.

58. 1-(3-Chlorophenyl)-3-methylaza-7-cyano-7-(1,3-benzodioxan-6-yl)-nonadecane

Analysis: Calculated: C 73.8; H 8.9; N 5.1; Cl 6.4. Found: C 73.7; H 8.8; N 5.2; Cl 6.4.

59. 1-(3-Trifluoromethylphenyl)-3-methylaza-7-cyano-7-(3-methoxyphenyl)-nonadecane Analysis: Calculated: C 73.0; H 8.8; N 5.0. Found: C 73.2; H 8.8; N 5.0.

60. 1-(3-Chlorophenyl)-3-methylaza-7-cyano-7-(3,4-dimethoxyphenyl)-nonadecane

Analysis: Calculated: C 73.5; H 9.3; N 5.0; Cl 6.4. Found: C 73.7; H 9.2; N 4.9; Cl 6.5.

61. 1-(3,5-Dimethoxyphenyl)-3-methylaza-7-cyano-7-(3-trifluoromethylphenyl)-nonadecane Analysis: Calculated: C 71.4; H 8.7; N 4.8. Found: C 71.6; N 9.0; N 4.8.

62. 1-(3,4-Methylenedioxyphenyl)-3-methylaza-7-cyano-7-(3,4-dimethoxyphenyl)-nonadecane Analysis: Calculated: C 74.4; H 9.3; N 5.0. Found: C 74.6; H 9.2; N 5.1.

63. 1-(3,4-Ethylenedioxyphenyl)-3-methylaza-7-cyano-7-(3-methoxyphenyl)-nonadecane Analysis: Calculated: C 76.6; H 9.6; N 5.1. Found: C 76.7; H 9.6; N 5.1.

64. 1-(1,3-Benzodioxan-6-yl)-3-methylaza-7-cyano-7-(3,5-diethoxyphenyl)-nonadecane Analysis: Calculated: C 75.2; H 9.6; N 4.6. Found: C 75.1; H 9.5; N 4.8.

65. 1-(3-Nitrophenyl)-3-methylaza-7-cyano-7-(3-methoxyphenyl)-nonadecane

Analysis: Calculated: C 74.0; H 9.2; N 7.8. Found: C 74.1; H 9.1; N 7.9.

66. 1,7-bis-(3,5-Diethoxyphenyl)-3-methylaza-7-cyano-nonadecane

Analysis: Calculated: C 75.1; H 10.1; N 4.4. Found: C 75.5; H 10.0; N 4.4.

EXAMPLES 67 TO 73

Reductive amination of α-alkyl-α-(γ-oxopropyl)-phenylacetonitriles with N-methyl-β-phenethylamines 0.5 mole of the corresponding α-alkyl-α-(γ-oxopropyl)-phenylacetonitrile (prepared from the α-alkylphenylacetonitrile and β-chloropropionaldehyde diethyl acetal in the presence of lithium diisopropylamide and subsequent liberation of the aldehyde with aqueous oxalic acid solution) and 0.5 mole of N-alkyl-β-phenethylamine were dissolved in 500 ml of toluene. 0.55 mole of formic acid (98–100% strength) was added in the cold. The reaction mixture was refluxed until the evolution of gas subsided.

Aqueous potassium carbonate solution was added to the cooled reaction solution and the amine liberated was extracted with an ether/hexane mixture and then removed therefrom with aqueous amidosulfonic acid. The amidosulfonate solution was extracted several times with ether to remove neutral constituents, and the base was liberated with potassium carbonate solution and extracted with ether. After being dried with potassium carbonate under reduced pressure, the ethereal solution was distilled and the oily residue was purified by salt formation and crystallization or by column chromatography (silica gel, ethyl acetate). The yields were about 85%.

The compounds which follow were prepared by this process:

67. 1-(4-Chlorophenyl)-3-methylaza-7-cyano-7-(3-methoxyphenyl)-nonadecane hydrochloride of melting point 89°–90° C.

68. 1-(3,5-Diethoxyphenyl)-3-methylaza-7-cyano-7-(3-ethoxyphenyl)-docosane hydrochloride of melting point 80°–83° C.

69. 1-(3,5-Dimethoxyphenyl)-3-methylaza-7-cyano-7-(3-ethoxyphenyl)-docosane hydrochloride of melting point 83°–86° C.

70. 1-(3,5-Dimethoxyphenyl)-3-methylaza-7-cyano-7-(3-ethoxyphenyl)-nonadecane hydrochloride of melting point 82°–85° C.

71. 1-(3,4,5-Trimethoxyphenyl)-3-methylaza-7-cyano-7-(3-ethoxyphenyl)-docosane hydrochloride of melting point 119°–120° C.

72. 1-(3,4,5-Trimethoxyphenyl)-3-methylaza-7-cyano-7-(3-ethoxyphenyl)-nonadecane hydrochloride of melting point 116°–118° C.

73. 1-(3,5-Diethoxyphenyl)-3-methylaza-7-cyano-7-(3-ethoxyphenyl)-nonadecane hydrochloride of melting point 77°–79° C.

EXAMPLE 74

1,7-bis-(3-Methoxyphenyl)-3-aza-7-cyano-eicosane 37 g of α-tridecyl-α-(γ-oxopropyl)-3-methoxyphenyl-acetonotrile and 15 g of β-(3-methoxyphenyl)ethylamine were dissolved in 500 ml of toluene, and the solution was refluxed until no further separation of water could be detected in the water separator. The toluene was then distilled off, the oily residue was dissolved in 500 ml of methanol, and 3.8 g of sodium borohydride were added at room temperature, with stirring. Stirring was continued for 5 hours, water was added, the mixture was extracted with a mixture of ether and hexane and the extract was shaken with aqueous amidosulfonic acid solution. The amidosulfonic acid phase was separated off and rendered alkaline with aqueous potassium carbonate solution, and the base which separated out was extracted with ether. The extract was dried with potassium carbonate, the ether was distilled off and the oily residue was purified by column chromatography (silica gel, ethyl acetate).

Analysis: Calculated: C 78.4; H 10.1; N 5.4. Found: C 78.5; H 10.0; N 5.2.

The compound which follows was obtained in a similar manner:

75. 1,7-bis-(3-Methoxyphenyl)-3-aza-7-cyano-nonadecane hydrogen oxalate of melting point 121°–123° C.

EXAMPLE 76

1,8-Diphenyl-3-methylaza-8-cyano-eicosane

A mixture of 0.5 mole of α-dodecyl-α,σ-methylaminobutyl)-phenyl-acetonitrile (prepared by reacting α-dodecyl-phenylacetonotrile and 4-methylformamido-1-chlorobutane in the presence of sodium hydride and then splitting off the formyl group by means of hydrochloric acid), 0.5 mole of phenylacetaldehyde, 2 g of 5% strength palladium-on-charcoal and 500 ml of toluene was subjected to catalytic reduction under atmospheric pressure at from 25° to 30° C. for 20 hours. After the catalyst had been removed, the base was extracted with aqueous amidosulfonic acid solution, the acid solution was washed with ether and the base was liberated again with aqueous potassium carbonate solution and extracted with ether. The extract was dried with potassium carbonate and the ether was then distilled off. The resulting base was purified by column chromatography (silica gel, ethyl acetate).

Analysis: Calculated: C 83.5; H 10.6; N 5.9. Found: C 83.4; H 10.3; N 5.7.

The compound which follows was obtained in a similar manner:

77. 1,8-Diphenyl-4-methylaza-8-cyano-eicosane.

Analysis: Calculated: C 83.5; H ;b 10.6; N 5.9. Found: C 83.7; H 10.4; N 5.7.

EXAMPLE 78

(+)-1,7-bis-(3-Methoxyphenyl)-3-methylazo-7-cyano-nonadecane 38.7 g (0.1 mole) of 4-cyano-4-(3-methoxyphenyl)-hexadecanecarboxylic acid (melting point 36°–38° C., prepared by adding acrylonitrile to α-dodecyl-3-methoxybenzylcyanide and subsequent saponification) were dissolved with 29.4 g (0.1 mole) of cinchonine in 200 ml of methanol. After some time the salt of the dextrorotatory acid crystallized out and this was suction filtered and recrystallized several times from 3 parts of methanol until a constant rotation value was obtained. The yield, after the salt had been recrystallized twice, was 12 g (35%), melting point 125°–127° C., $[\alpha]_{589}^{20}nm = +98°$ (ethanol, C=10 mg/ml). The free dextrorotatory acid, melting point 41° C., $[\alpha]_{589}^{20}nm = +15°$ (ethanol, C=15 mg/ml) is obtained from the salt in conventional manner.

By reaction with ethyl chloroformate, the acid was converted to the mixed anhydride which was reduced in good yield with sodium borohydride to (+)-4-(3-methoxyphenyl)-4-cyano-1-chlorohexadecane. Both reactions were carried out as described in German Pat. Nos. 2,059,923 and 2,059,985.

5 g (0.0128 mole) of crude (+)-4-(3-methoxyphenyl)-4-cyano-1-chlorohexadecane were then heated for 1 h at 160° C. with 4.2 g (0.0254 mole) of N-methyl-3-methoxyphenethylamine, ether was added to the cold reaction mixture, which was suction filtered from the hydrochloride that separated out, and the solution was washed with water, dried and evaporated. The residue was purified by column chromatography (silica gel, ethyl acetate). The yield was 4.8 g (69.5%) of a yellowish oil, Rf=0.8 (CH$_2$Cl/methanol 9:1), 0.2 (hexane/ethyl acetate 6:4), $[\alpha]_{589}^{20}nm = +7°$ (benzene, C=30 mg/ml).

EXAMPLE 79

(−)-1,7-bis-(3-Methoxyphenyl)-3-methylaza-7-cyano-nonadecane

The levorotatory acid (−)-4-cyano-4-(3-methoxyphenyl)hexadecanecarboxylic acid was obtained in poor optical purity from the mother liquors of the 1st stage of Example 78. It was allowed to crystallize in brucine in 90% strength aqueous methanol, the brucine salt of the levorotatory acid being obtained, which was also recrystallized until a constant rotation value was obtained. The melting point was 61° C., $[\alpha]_{589}^{20}nm = 15.5°$ (ethanol, C=10 mg/ml).

The levorotatory acid was isolated pure from this: melting point 41° C., $[\alpha]_{589}^{20}nm = 16°$ (ethanol, C=10 mg/ml).

The further synthesis steps were carried out as described in Example 78. The properties of the desired compound, with reference to the specific rotation value $[\alpha]_{589}^{20}nm = -7°$ (benzene, C=30 mg/ml), agreed with the enaniomorphs described in Example 78.

EXAMPLE 80

1,7-bis-(3-Hydroxyphenyl)-3-methylaza-7-cyano-nonadecane 200 ml of anhydrous trifluoroacetic acid were poured over 60.5 g (0.1 mole) of 1,7-bis-(3-tert.-butoxyphenyl)-3-methylaza-7-cyano-nonadecane (Example 38) and the whole was allowed to stand for 4 h at room temperature. The trifluoroacetic acid was then distilled off in vacuo, 500 ml of water were added to the residue and the base was liberated with ammonia. The base was taken up in 200 ml of ether, washed with water and dried with magnesium sulfate. After the ether had been distilled off, the base obtained as an oily residue was chromatographed on silica gel using ethyl acetate/methanol (95:5).

Analysis: Calculated: C 78.0; H 9.8; N 5.7. Found: C 77.8; H 9.7; N 5.6.

The compounds which follow were obtained in a similar manner:

81. 1-(3-Methoxyphenyl)-3-methylaza-7-cyano-7-(3-hydroxyphenyl)-nonadecane

Analysis: Calculated: C 78.2; H 9.9; N 5.5. Found: C 78.3; H 9.8; N 5.4.

82. 1-(3-Hydroxyphenyl)-3-methylaza-7-cyano-7-(3-methoxyphenyl)-nonadecane

Analysis: Calculated: C 78.2; H 9.9; N 5.5. Found: C 78.1; H 9.7; N 5.5.

EXAMPLE 83

1-(3-Nitro-4-methoxyphenyl)-3-methylaza-7-cyano-7-(3-methoxyphenyl)-nonadecane 20.0 g (0.054 mole) of N-methyl-4-cyano-4-(3-methoxyphenyl)-hexadecylamine (hydrochloride: melting point 112°–114° C.), 5.8 g (0.027 mole) of 3-nitro-4-methoxyphenethyl chloride and 0.25 g of sodium iodide in a solvent mixture of 50 ml of acetonitrile and 10 ml of dimethylsulfoxide were heated at 50°–55° C. for 60 hours. 100 ml of water were added, the reaction solution was rendered alkaline with ammonia and the base was then extracted with a mixture of 350 ml of n-hexane and 50 ml of ether. The solvent was distilled off and the base obtained as the oily residue was chromatographed on silica gel using ethyl acetate.

Analysis: Calculated: C 72.2; H 9.1; N 7.4. Found: C 72.1; H 9.0; N 7.5.

The compound which follows was obtained in a similar manner:

84. 1-(2-Chlorophenyl)-3-methylaza-7-cyano-7-(3-methoxyphenyl)-nonadecane

Analysis: Calculated: C 75.5; H 9.4; N 5.3; Cl 6.8. Found: C 75.5; H 9.3; N 5.5; Cl 6.9.

EXAMPLE 85

1-(3-Methoxyphenyl)-3-methylaza-7-cyano-7-(3,4,5-trimethoxyphenyl)-eicosane 20.7 g (0.1 mole) of 3,4,5-trimethoxyphenylacetonitrile were dissolved in 15 ml of toluene at 40° C., and 52 g (0.8 mole) of 85% pure potassium hydroxide powder and 0.2 g of tetrabutylammonium iodide were added. A solution of 26.3 g (0.1 mole) of tridecyl bromide in 20 ml of toluene was then added, with stirring, so that the temperature did not exceed 90° C. After the addition, stirring was continued at this temperature for 2 hours, and a solution of 24.2 g (0.1 mole) of 1-chloro-4-methylaza-6-(3-methoxyphenyl)-hexane in 20 ml of toluene was then added at 90° C. The reaction mixture was stirred at 90° C. for a further 3 hours and cooled, 100 ml of water were added and the toluene phase was separated off. The solvent was distilled off to give the crude base as a yellow oil, which was chromatographed on silica gel using ethyl acetate.

Rf value (methylene chloride/methanol=93:7): 0.44.
Analysis: Calculated: C 74.7; H 9.8; N 4.7. Found: C 74.7; H 9.4; N 4.8.

EXAMPLE 86

1-(3-Methoxyphenyl)-3-methylaza-7-cyano-7-(3,4-dimethoxyphenyl)-eicosane 38.3 g (0.1 mole) of 1-(3-methoxyphenyl)-3-methylaza-7-cyano-7-(3,4-dimethoxyphenyl)-heptane were dissolved in 200 ml of toluene, and the solution was refluxed with 4.7 g (0.12 mole) of powdered sodium amide for 1 hour, with stirring. A solution of 26.3 g (0.1 mole) of tridecyl bromide in 50 ml of toluene was then added dropwise in the course of 60 minutes, and the mixture was refluxed for a further 2 hours. The cooled reaction mixture was poured into water, the toluene phase was washed several times with water, and the toluene was then distilled off. The resulting residue was chromatographed on silica gel using ethyl acetate.

Rf value (methylene chloride/methanol=93:7): 0.44.
Analysis: Calculated: C 76.6; H 10.0; N 5.0. Found: C 76.4; H 9.3; N 5.0.

EXAMPLE 87

1,7-bis-(3-Methoxyphenyl)-3-methylaza-7-cyano-eicosane 52.1 g (0.1 mole) of the compound obtained in Example 66 were dissolved in 23 g (0.5 mole) of formic acid in the cold, 11.9 ml of 35% strength aqueous formalin solution (0.15 mole of formaldehyde) were added, and the mixture was heated on a waterbath until evolution of carbon dioxide had ended. The reaction solution was cooled, diluted with water and rendered alkaline by addition of ammonia, and the base which had separated out was extracted with n-hexane. The n-hexane solution was washed several times with water and dried with potassium carbonate, and the n-hexane was then distilled off. The residue was chromatographed on silica gel (ethyl acetate/n-hexane=7:3) and the main fraction was concentrated to give the base as a viscous oil.

Rf value (methylene chloride/methanol=97:7): 0.53.
Analysis: Calculated: C 78.6; H 10.2; N 5.2. Found: C 78.5; H 10.1; N 5.1.

EXAMPLE 88

Tablets of the following composition were obtained on a tableting machine in a conventional manner:
40 mg of the substance from Example 3
120 mg of corn starch
13.5 mg of gelatine
45 mg of lactose
2.25 mg of Aerosil ® (chemically pure silicic acid in submicroscopically fine division)
6.75 mg of potato starch (as 6% strength paste)

EXAMPLE 89

Coated tablets of the following composition were prepared in a conventional manner:
20 mg of the substance from Example 3
60 mg of core composition
60 mg of sugar-coating composition The core composition consisted of 9 parts of corn starch, 3 parts of lactose and 1 part of Luviskol ® VA 64 (60:40 vinylpyrrolidone/vinyl acetate copolymer, cf. Pharm. Ind. 1962, 586). The sugar-coating composition consisted of 5 parts of sucrose, 2 parts of corn starch, 2 parts of calcium carbonate and 1 part of talc. The coated tablets thus obtained were then provided with a further coating which was resistant to gastric juice.

EXAMPLE 90

10 g of the substance from Example 3 were dissolved in 5000 ml of water, with the addition of NaCl, and the solution was brought to pH 6.0 with 0.1 N NaOH to form a solution isotonic with blood. This solution was introduced into ampoules, 5 ml in each, and sterilized.

We claim:

1. An ω-cyano-1,ω-diphenyl-azaalkane derivative of the formula I,

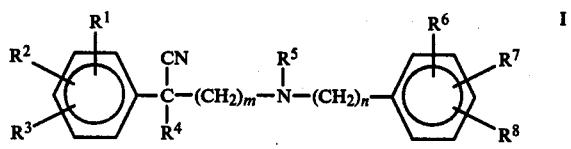

where $R^1$, $R^2$, $R^3$, $R^6$, $R^7$ and $R^8$ are identical or different and each is hydrogen, halogen, hydroxyl, trifluoromethyl, $C_1$–$C_4$-alkyl, nitro, $C_1$–$C_4$-alkoxy or $C_1$–$C_4$-alkylmercapto, and two radicals in adjacent positions can together form a methylenedioxy, ethylenedioxy or 1,3-dioxatetramethylene group, $R^4$ is straight-chain or branched, saturated or unsaturated alkyl of 9 to 20 carbon atoms, $R^5$ is hydrogen or $C_1$–$C_4$-alkyl and m and n are identical or different and each is from 2 to 4, and salts thereof with a physiologically tolerated acid.

2. 1,7-bis-(3-Methoxyphenyl)-3-methylaza-7-cyano-nonadecane.

3. 1-(3-Methoxyphenyl)-3-methylaza-7-cyano-7-(3,4-dimethoxyphenyl)-nonadecane.

4. 1-(3-Methoxyphenyl)-3-methylaza-7-cyano-7-(3,4,5-trimethoxyphenyl)-nonadecane.

5. 1,7-Diphenyl-3-methylaza-7-cyano-nonadecane.

6. An ω-cyano-1,ω-diphenyl-azaalkane derivative of the formula I as set forth in claim 1, wherein $R^1$, $R^2$, $R^3$, $R^6$, $R^7$, and $R^8$ are hydrogen or alkoxy; $R^4$ is a straight-chain alkyl of 10 to 14 carbon atoms; and $R^5$ is methyl.

7. An ω-cyano-1,ω-diphenyl-azaalkane derivative of the formula I as set forth in claim 1, wherein n+m is 5.

8. An ω-cyano-1,ω-diphenyl-azaalkane derivative of the formula I as set forth in claim 6, wherein n+m is 5.

9. An ω-cyano-1,ω-diphenyl-azaalkane derivative of the formula I as set forth in claim 1, wherein $R^1$, $R^2$, $R^3$, $R^6$, $R^7$, and $R^8$, are hydrogen or methoxy; $R^4$ is a straight-chain alkyl of 10 to 14 carbon atoms; and $R^5$ is methyl.

10. An ω-cyano-1,ω-diphenyl-azaalkane derivative of the formula I as set forth in claim 9, where n+m is 5.

11. An ω-cyano-1,ω-diphenyl-azaalkane derivative of the formula I as set forth in claim 6, wherein $R^4$ is a straight-chain alkyl of 11 to 13 carbon atoms.

12. An ω-cyano-1,ω-diphenyl-azaalkane derivative of the formula I as set forth in claim 11, wherein n+m is 5.

13. An ω-cyano-1,ω-diphenyl-azaalkane derivative of the formula I as set forth in claim 12, wherein $R^1$, $R^2$, $R^3$, $R^6$, $R^7$, and $R^8$ are hydrogen or methoxy.

14. A therapeutic composition for treating cardiovascular disorders comprising a pharmaceutical excipient and an effective amount of an ω-cyano-1,ω-diphenyl-azaalkane derivative of the formula I according to claim 1 as the active ingredient.

15. The method of treating cardiovascular disorders in a patient suffering therefrom which comprises administering an effective amount of an ω-cyano-1,ω-diphenyl-azaalkane derivative of the formula I according to claim 1.

* * * * *

UNITED STATES PATENT AND TRADEMARK OFFICE
CERTIFICATE OF CORRECTION

PATENT NO. : 4,438,131

DATED : March 20, 1984

INVENTOR(S) : Oskar EHRMANN et al.

It is certified that error appears in the above-identified patent and that said Letters Patent is hereby corrected as shown below:

IN THE TITLE

The title should be --$\omega$-CYANO-1, $\omega$-DIPHENYL-AZAALKANE DERIVATIVES, THEIR PREPARATION AND DRUGS CONTAINING THEM -- rather than "$\Omega$-CYANO-1, $\Omega$-DIPHENYL-AZAALKANE DERIVATIVES, THEIR PREPARATION AND DRUGS CONTAINING THEM"

Signed and Sealed this

Second Day of October 1984

[SEAL]

Attest:

GERALD J. MOSSINGHOFF

Attesting Officer     Commissioner of Patents and Trademarks